(12) United States Patent
Crook

(10) Patent No.: US 8,446,274 B1
(45) Date of Patent: May 21, 2013

(54) LONE WORKER GAS SAFETY ALARM SYSTEM AND METHOD

(76) Inventor: Gary W. Crook, Midland, TX (US)

( * ) Notice: Subject to any disclaimer, the term of this patent is extended or adjusted under 35 U.S.C. 154(b) by 316 days.

(21) Appl. No.: 13/065,137

(22) Filed: Mar. 15, 2011

Related U.S. Application Data

(60) Provisional application No. 61/458,389, filed on Nov. 23, 2010.

(51) Int. Cl.
G08B 1/08 (2006.01)
(52) U.S. Cl.
USPC .............. 340/539.11; 340/539.17; 340/573.1; 340/632
(58) Field of Classification Search
USPC .............. 340/539.11, 539.16, 539.17, 573.1, 340/632
See application file for complete search history.

(56) References Cited

U.S. PATENT DOCUMENTS

| 5,568,121 | A  | * | 10/1996 | Lamensdorf    | 340/539.17 |
| 5,742,233 | A  |   | 4/1998  | Hoffman et al. |            |
| 6,744,373 | B2 | * | 6/2004  | Koyano et al. | 340/693.5  |
| 6,856,253 | B1 | * | 2/2005  | Crook         | 340/632    |
| 7,412,264 | B2 |   | 8/2008  | Swallow       |            |
| 7,832,132 | B2 |   | 11/2010 | McLachlan     |            |
| 8,330,605 | B2 | * | 12/2012 | Johnson et al. | 340/632   |
| 2008/0276506 | A1 | | 11/2008 | McLachlan     |            |

* cited by examiner

Primary Examiner — Toan N Pham
(74) Attorney, Agent, or Firm — www.bobharter.com; Robert J. Harter

(57) ABSTRACT

A person-carried portable transceiver unit informs a remote home base of the person's activities, location, and/or exposure to a toxic gas. The person uses the portable transceiver unit for sending different predetermined chosen text messages to the home base. In some examples, the particular message is chosen by the number of times the person sequentially triggers a single switch on the unit. In cases where the single switch is a pushbutton, pressing the button three times, for example, could indicate the person is heading to a worksite, and pressing the button four times could indicate the person arrived at the worksite. For the home base to determine whether the person is still conscious and alert while at the worksite, the home base periodically sends to the portable unit reminder signals that prompt the person for a certain response, such as, for example, the person pressing the button twice in succession.

23 Claims, 4 Drawing Sheets

LONE WORKER GAS SAFETY ALARM SYSTEM AND METHOD

CROSS REFERENCE TO RELATED APPLICATIONS

This application claims the benefit of provisional patent application Ser. No. 61/458,389 filed on Nov. 23, 2010 by the present inventor.

FIELD OF THE DISCLOSURE

The subject invention generally pertains to personal monitor systems and more particularly to systems that communicate with a remote home base.

BACKGROUND

Working alone can be dangerous in certain situations. Assigning two or more workers that can watch out for each other might be safer, but in some cases such an approach might subject more workers than necessary to a hazardous environment. Various personal monitors and alarm systems have been developed, but they seem to fall short in one or more areas including, but not limited to, failing to distinguish between when a person is in a relatively safe environment or a more hazardous one.

DETAILED DESCRIPTION

Figure 1:
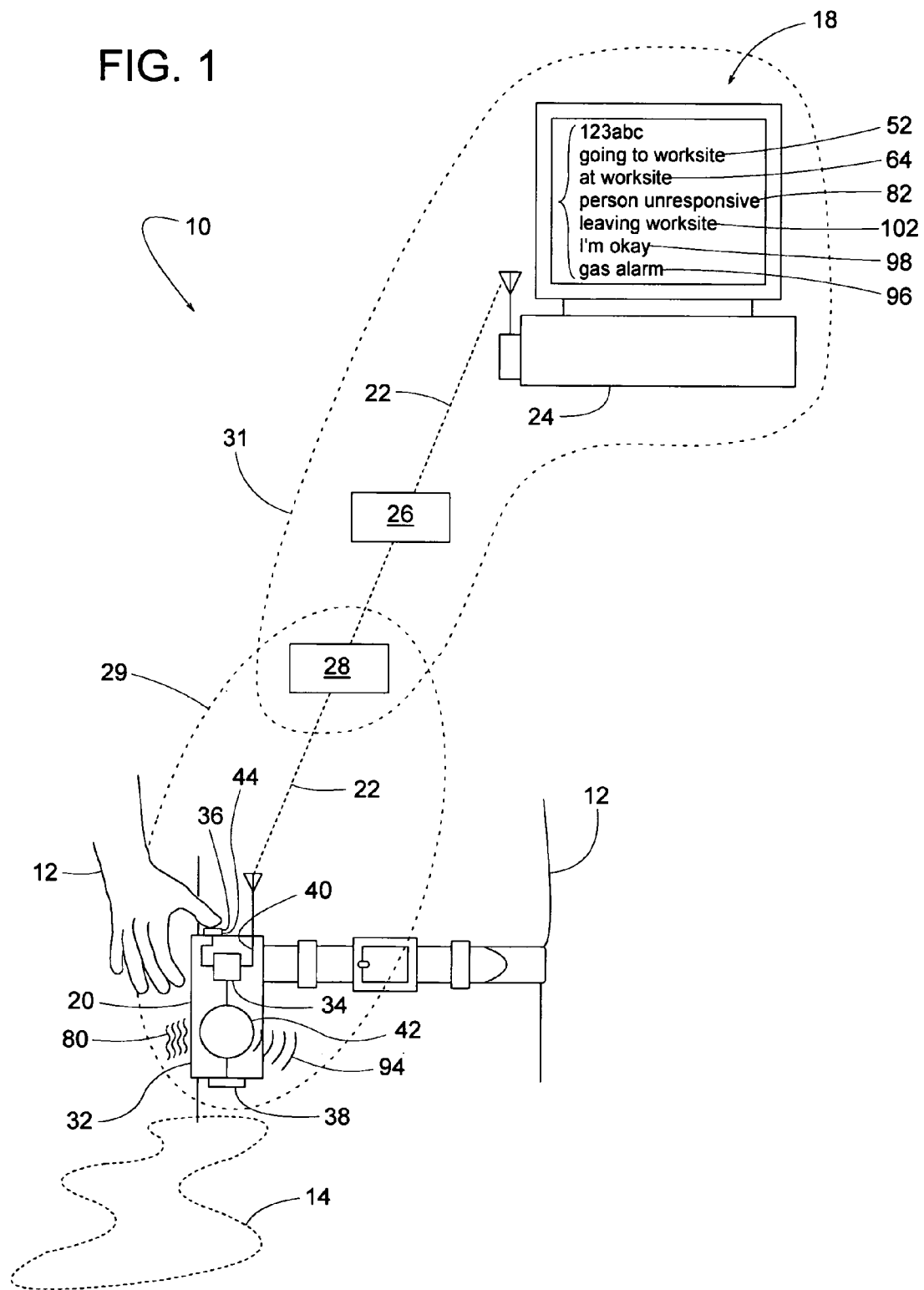
FIG. 1 is a schematic diagram of one example of a personal monitor system and method.
Figure 2:
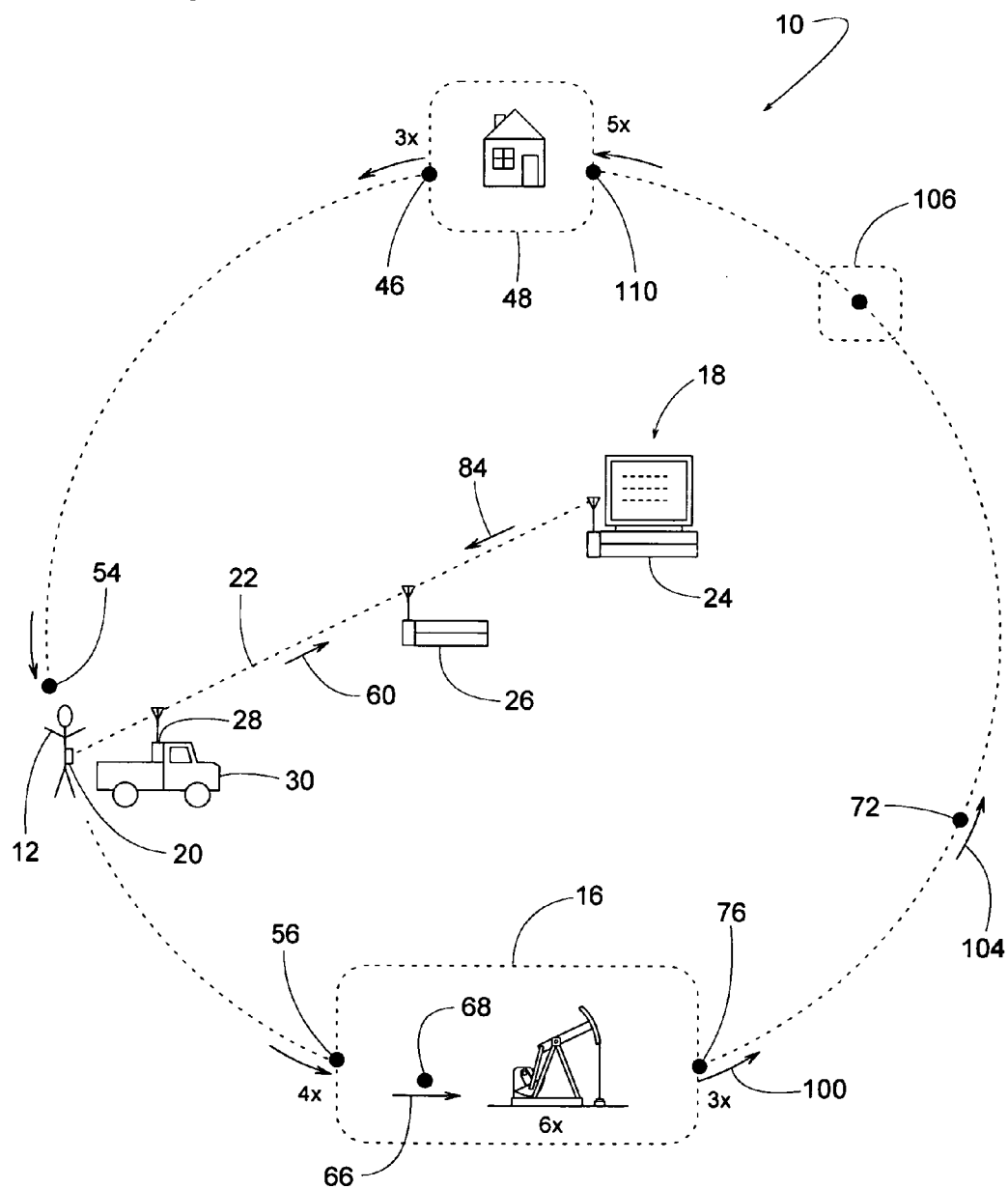
FIG. 2 is a schematic diagram illustrating an example method for using the personal monitor system of FIG. 1.
Figure 3:
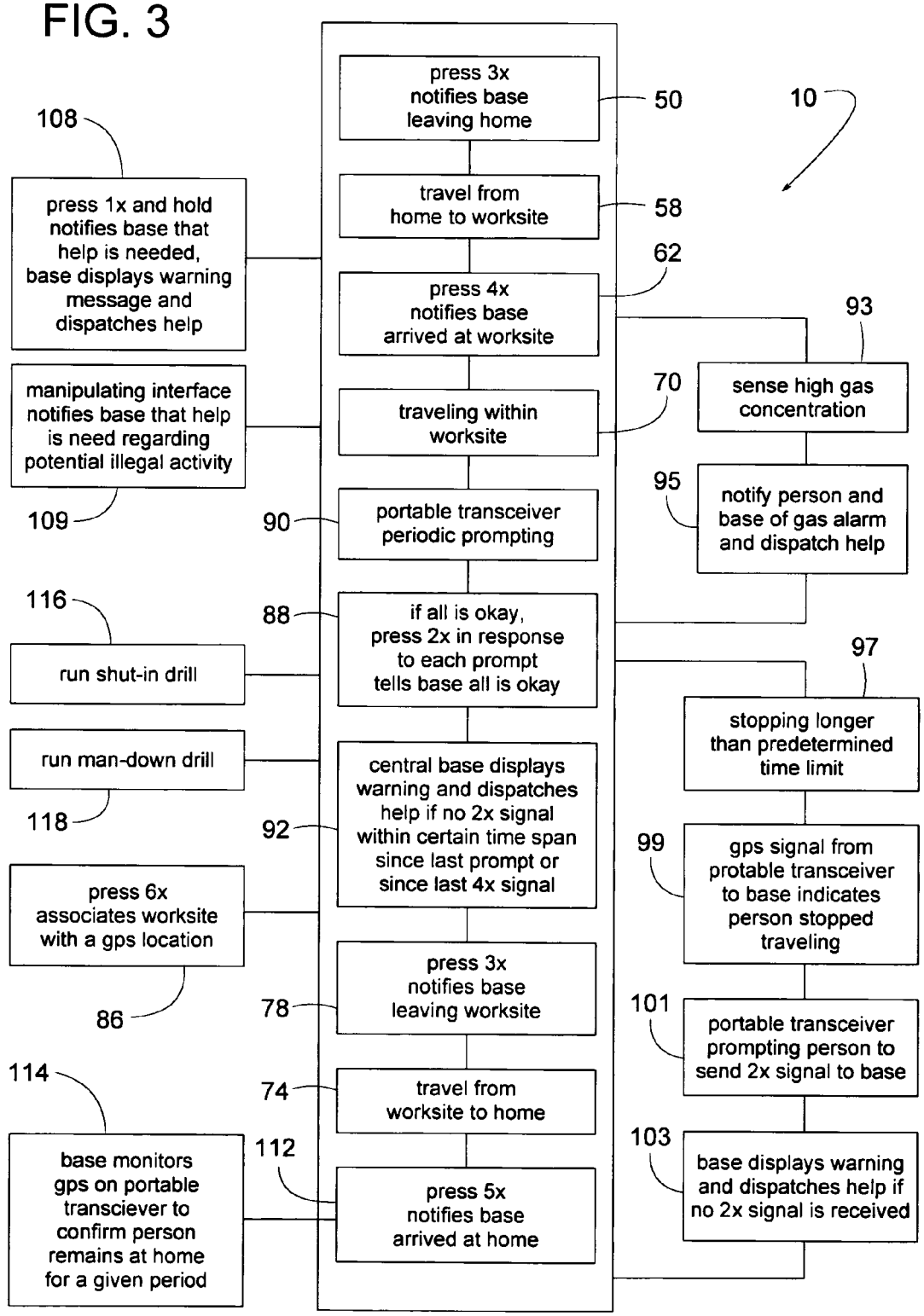
FIG. 3 is a block diagram illustrating one example of various steps performed by a central base, by the person and by the logic circuit of the personal monitor system.

FIGS. 1-3 illustrate a personal monitor system/method 10 for monitoring the safety of a person 12 such as a lone worker that might be exposed to a hazardous gas 14 (e.g., hydrogen sulfide) or exposed to other hazards while either at a worksite 16 (e.g., a well site) or while traveling to or from worksite 16. In some examples, personal monitor system 10 comprises a central base system 18 and a portable transceiver unit 20 carried by person 12 and being movable thereby to a remote location relative to central base system 18. The term, "remote" means that personal monitor system 10 is still functional when portable transceiver unit 20 is at least ten miles away from the most distant component of base 18, thus personal monitor system 10 is not limited to being contained within a single building.

Central base system 18 is schematically illustrated to represent any system adapted for exchanging signals (e.g., text messages, alarms, data, information, commands, inquiries, feedback, etc.) with portable transceiver unit 20 via a wireless communication link 22. Examples of central base system 18 and components thereof include, but are not limited to, a computer 24, a server 26, a supplemental communication/logic circuit 28, a website, a wireless modem, a cell phone, a satellite phone, software, a laptop computer, a smart phone with an operating application, a desktop computer, and various combinations thereof. The expression, "wireless communication link" refers to conveying information, data, etc., that at some point passes through air or space via electromagnetic radiation, e.g., microwave, radio wave, etc. with assistance from some sort of receiver/transmitter, e.g., satellite, antenna, cell phone tower, etc.

Supplemental communication/logic circuit 28 is schematically illustrated to represent any device that helps process data, collect data and/or facilitate the communication between base 18 and portable transceiver 20. In some examples, one or more components of supplemental communication/logic circuit 28 are an integral part of portable transceiver 20, as indicated by dashed line 29. In some examples, one or more components of supplemental communication/logic circuit 28 are part of central base system 18, as indicated by dashed line 31. In some examples, components of supplemental communication/logic circuit 28 are divided between portable transceiver 20 and base system 18. In still other examples, supplemental communication/logic circuit 28 is a separate item in wireless communication with portable transceiver 20 and base 18. For the illustrated example, supplemental communication/logic circuit 28 is a circuit carried by a vehicle 30 that person 12 uses for traveling to and from worksite 16, wherein circuit 28 includes an eSOM270 Marvell (formally Intel) XScale PXA270 processor based computer on module provided by e-con Systems, Inc. of Chennai area, India. For acquiring location coordinates, circuit 28 also includes a GPS receiver (e.g., a BC-337 SiRF Star III provided by GlobalSat of Brussels area, Belgium. For communicating with portable transceiver unit 20, circuit 28 includes a model CC110X transceiver (and its associated conventional electrical components and connections) by Texas Instruments. For communicating with base 18, circuit 28 includes a Q9612 modem by Quake Global, Inc. of San Diego, Calif. Supplemental communication/logic circuit 28 being separate from portable transceiver unit 20 makes portable transceiver unit 20 smaller and more lightweight. The term, "portable," as used with the expression, "portable transceiver unit," means that such a transceiver unit has its own onboard power supply (e.g., a battery, power storage capacitor, etc.) and can be readily carried by person 12, i.e., portable transceiver unit 20 weighs less than 2 pounds.

Portable transceiver unit 20 is a personal monitor that includes a housing 32 containing and/or supporting a plurality of components, whereby the plurality of components are borne by the portable transceiver unit. Examples of such components include a logic circuit 34 for receiving and processing inputs and providing outputs in response thereto per code stored on logic circuit 34, a user interface 36 being operatively coupled to logic circuit 34 and being responsive to a plurality of manual manipulations by person 12, a gas sensor 38 operatively coupled to logic circuit 34 and being responsive to various concentrations of gas 14, a transceiver circuit 40 operatively coupled to logic circuit 34 to place portable transceiver 20 in communication with base 18 (directly or via intermediate links such as, for example, supplemental communication/logic circuit 28, server 36, cell phone towers, satellites, modems, and various combinations thereof, etc.), and a notification system 42 operatively coupled to logic circuit 34. Examples of notification system 42 comprise one or more of the following: a speaker(s), a vibrator(s), a buzzer(s), a light(s), a display screen(s), etc.

An example of logic circuit 34 includes, but is not limited to, a model MSP430XG461XIPZ (and its associated conventional electrical components and connections) by Texas Instruments of Dallas, Tex. Other examples of logic circuit 34 include other models within the MSP430 family of Texas Instrument microcontrollers. Still other examples of logic circuit 34 include, but are not limited to, a computer, a microprocessor, an integrated circuit, a PLC, etc.

Examples of user interface 36 include, but are not limited to, a pushbutton 44, multiple pushbuttons, a toggle switch, a touch screen, a proximity switch, and any of a variety of other types of switches. The expression, "manual manipulation" refers to any means associated with interface 36 for a user to physically input a signal into portable transceiver unit 20. Examples of manual manipulation include, but are not limited to, pushing, pulling, touching, turning, tilting, etc. An example of gas sensor 38 includes, but is not limited to, a model H2S-D1 (and its associated conventional electrical components and connections) by Alphasense of Great Notley, UK. An example of transceiver circuit 40 includes, but is not limited to, a model CC110X transceiver (and its associated conventional electrical components and connections) by Texas Instruments. Examples of notification circuit 42 include, but are not limited to, a buzzer, a speaker, a vibrator, a light, and various combinations thereof.

Referring to FIGS. 2 and 3, an example method involving personal monitor system 10 is as follows. In this example, portable transceiver unit 20 is attached to person 12, thereby maintaining portable transceiver unit 20 in proximity with person 12 such that portable transceiver unit 20 and person 12 generally travel and move with each other as a unit. Supplemental communication/logic circuit 28, in this example, is installed in vehicle 30 for gathering and providing location information (e.g., GPS coordinates), facilitating communication between portable transceiver unit 20 and base 18, and/or for other reasons. In this example, supplemental communication/logic circuit 28 is heavier and bulkier than portable transceiver unit 20, thus only portable transceiver unit 20 is carried by person 12.

In this particular example, the method of using personal monitor system 10 during a chosen period of monitoring begins at a point 46 where person 12 with portable transceiver unit 20 first leaves the person's predetermined home location 48 (e.g., the person's residence). At point 46, person 12 pushes button 44 three times in succession (e.g., three times or some other predetermined given number of times within a certain limited time span such as, for example, within three seconds). This notifies central base 18, via communication link 22, that person 12 is leaving home and heading for worksite 16 (block 50 of FIG. 3), so base 18 displays a text message 52 (a record) indicating that.

As person 12 and portable transceiver 20 travel from point 46, through an intermediate point 54 and to a point 56 (block 58 of FIG. 3), communication link 22 repeatedly conveys the changing location signal 60 (e.g., GPS signal) from supplemental communication/logic circuit 28 to base 18. Note, circuit 28 can be considered to be part of portable transceiver unit 20 even though the two may be spaced apart in some examples of the invention. Consequently, base 18 tracks and records the location of person 12 traveling to worksite 16.

At point 56, person 12 pushes button 44 four times in succession (or some other predetermined given number of times) to inform base 18 that person 12 has arrived at worksite 16 (block 62), and base 18 records and displays that information as a text message 64. In some examples, base 18 determines that person 12 is at worksite 16 based on location signal 60 at point 56. In other examples, base 18 determines that person 12 is at worksite 16 based on person 12 having pushed button 44 four times.

As person 12 travels within worksite 16, as indicated by an arrow 66 of FIG. 2, base 18 determines whether person 12 is traveling within worksite 16 (point 68 and block 70) or traveling beyond worksite 16 (e.g., points 54 and 72, and blocks 58 and 74). In some examples of the invention, base 18 determines whether person 12 is traveling within worksite 16 based on location signal 60 at point 68. In other examples, base 18 determines whether person 12 is still at worksite 16 based on the various signals created by person 12 pushing button 44. For example, person 12 pressing button 44 four times indicates person 12 has arrived at worksite 16, and later pressing button 44 three times (e.g., at point 76 of FIG. 2) indicates that person 12 is leaving worksite 16 (block 78).

While person 12 is at worksite 16, between points 56 and 76, personal monitor system 10 helps monitor the person's wellbeing. To do this, person 12 periodically presses button 44 twice in quick succession (check-in signal) to inform base 18 that person 12 is safe and okay (block 88 and message 98). After the first check-in signal, base 18 expects person 12 to repeat this action (subsequent check-in signal) every thirty minutes, or within some other predetermined or certain time span, so that base 18 can determine whether person 12 is still responsive and unharmed. In some examples, as indicated by block 90, portable transceiver unit 20 periodically emits a prompt signal 80 (audible, visible, vibration, etc.) that prompts or reminds person 12 to send another check-in signal (confirmation signal) when one is due. If base 18 does not receive an expected check-in signal (block 92), base 18 displays a warning message 82 (e.g., "person unresponsive"). In some examples, prompt signals 80 are initiated by supplemental/logic circuit 28. In some examples, prompt signals 80 are initiated by portable transceiver unit 20. In still other examples, prompt signals 80 are initiated by command signals 84 that wireless communication link 22 conveys from base 18.

In some examples, person 12 uses personal monitor system 10 to "tag" or identify the location of worksite 16. In some cases, for example, person 12 selectively presses push button 44 a given number of times (e.g., six times), thereby sending a location signal (e.g., GPS coordinates) from portable transceiver unit 20 via supplemental communication/logic circuit 28 to central base system 18, which in turn establishes and records an association of worksite 16 and the location signal, wherein the association is basically assigning GPS coordinates to a particular worksite name (block 86).

If sensor 38 senses gas 14 exceeding a predetermined level of concentration (block 93), portable transceiver unit 20 notifies person 12 of the problem by emitting an audible and/or visual alarm 94 (audible and/or visual), as indicated by block 95. Portable transceiver unit 20 also notifies base 18 of the problem, whereby system 10 displays an alarm message 96 (e.g., "gas alarm") so that assistance can be dispatched to the person's location.

In the illustrated example, person 12 informs base 18 when person 12 is departing worksite 16, as indicated by an arrow 100 of FIG. 2, by person 12 pressing button 44 three times (or some other given number of times), thereby generating message 102 of FIG. 1. In some examples, prompt signals 80 are reduced in frequency or discontinued entirely once system 10 determines that person 12 has left worksite 16. Person 12 can thus travel from worksite 16 to home location 48, as indicated by arrow 104 at point 72 in FIG. 2, without being interrupted excessively or unnecessarily by prompt signals 80.

If, however, person 12 stops at an intermediate or unexpected location 106 (e.g., a gas station at a generally fixed location) between worksite 16 and home 48, and remains there for a particularly long period (blocks 97 and 99), portable transceiver unit 20 emits prompt signal 80 (block 101) as a means for requesting that person 12 inform base 18 that person 12 is still okay. In response to prompt signal 80, person 12 can press push button 44 twice in succession to indicate that person 12 does not need any assistance. If person 12 does not respond to prompt signal 80, base 18 displays warning message 82 and dispatches assistance, as indicated by block 103. In some examples, person 12 at any time can call for help or request assistance by selectively pressing push button 44 a given number of times, wherein the given number is equal to at least one. In some examples, such a call for help is distinguishable from other push button signals by the given number or by pressing button 44 just once but holding button 44 down for a certain length of time (e.g., three seconds), as indicated by block 108.

In addition or alternatively to selectively manipulating the user interface (e.g., button 44) in a first manner (as indicated by block 108), person 12 at any time can manipulate the user interface 36 in a second manner (e.g., pressing button 44 a different number of times or pressing a different button of user interface 36 to trip a silent alarm conveyed to base 18), wherein the first manner (block 108) is for soliciting assistance related to a potential health problem (e.g., exposure to H2S gas) and the second manner (block 109) is for soliciting assistance related to a potential illegal activity (e.g., robbery, kidnapping or other crime).

In some examples, as indicated by blocks 116 and 118, method 10 is used for recording/documenting various drills performed at worksite 16. Examples of such drills include, but are not limited to a "shut-in" drill and a "man-down" drill. A so-called shut-in drill is practice in shutting down a well operation in response to an emergency such as sensing excessive H2S. Such a response or drill might involve sounding an H2S alarm and closing various valves (e.g., TIW valve, BOP valve, and casing valve). A man-down drill is practice in responding to an emergency where a person might be overcome by H2S gas. Such a response or drill might involve sounding an H2S alarm, one or more workers equipping themselves with SCBA (self contained breathing apparatus), rescuing the person needing help, and closing various valves.

Figure 4:
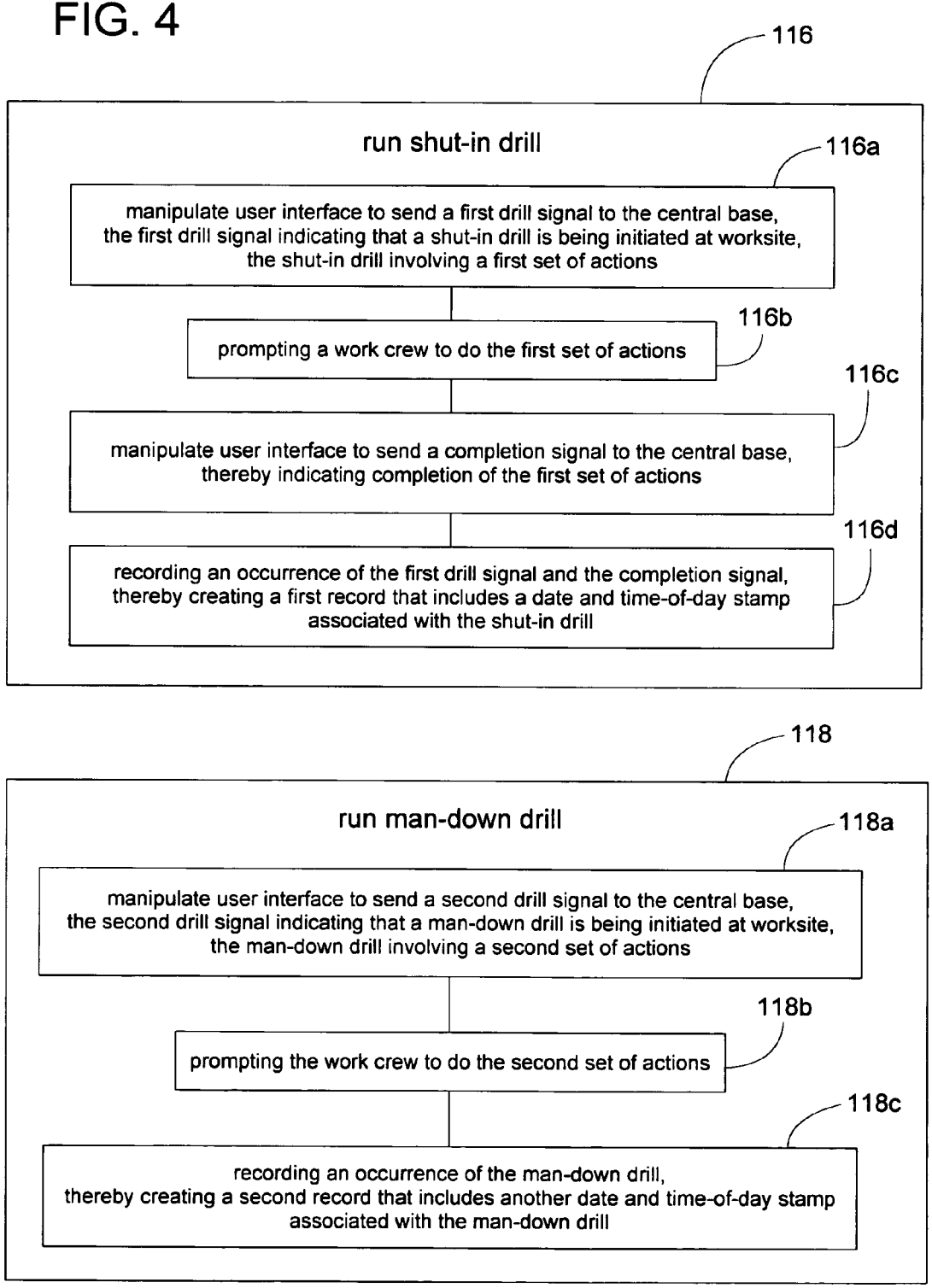
FIG. 4 is a block diagram illustrating additional steps of the block diagram shown in FIG. 3.

For illustration, FIG. 4 shows block 116 comprising blocks 116a, 116b, 116c and 116d. Block 116a illustrates manipulating user interface 36 to send (via link 22) a first drill signal to base 18, wherein the first drill signal indicates that a first drill (e.g., shut-in drill) is being initiated at worksite 16. As explained earlier, the first drill involves a first set of actions to be performed by a crew at worksite 16. Block 116b illustrates someone (e.g., a supervisor) prompting the crew to perform the first set of actions at worksite 16. Block 116c illustrates manipulating user interface 36 to send a completion signal (via link 22) to central base 18, wherein the completion signal indicates that the crew completed the first set of actions at worksite 16. Block 116d illustrates recording an occurrence of the first drill signal and the completion signal, thereby creating a first record (via text messages similar to messages 52, 64, 82, etc.) that includes a date and time-of-day stamp associated with the first drill (run-in drill).

For illustration, FIG. 4 shows block 118 comprising blocks 118a, 118b and 118c. Block 118a illustrates manipulating user interface 36 to send (via link 22) a second drill signal to base 18, wherein the second drill signal indicating that a second drill (e.g., man-down drill) is being initiated at worksite 16. As explained earlier, the second drill involves a second set of actions to be performed by the crew at worksite 16. The first drill being distinguishable from the second drill (shut-in drill vs. man-down drill) with the first set of actions (actions for the shut-in drill) being distinguishable from the second set of actions (actions for the man-down drill). Block 118b illustrates someone (e.g., a supervisor) prompting the crew to perform the second set of actions at worksite 16. Block 118c illustrates recording an occurrence of the second drill signal and creating a second record (via text messages similar to messages 52, 64, 82, etc.) that includes a second date and time-of-day stamp associated with the second drill (man-down drill).

Once person 12 returns home at point 110, as shown in FIG. 2, person 12 can inform base 18 by pressing button 44 five times (or some other given number of times), as indicated by block 112. After pressing push button 44 the given number of times to indicate that person 12 is at home location 48, system 10 determines (based on location signal 60) whether the portable transceiver unit 20 remains at home 48 or begins traveling beyond home location 48, as indicated by block 114. If person 12 remains at home 48, that completes the cycle until person 12 departs again for another worksite.

Although the invention is described with respect to a preferred embodiment, modifications thereto will be apparent to those of ordinary skill in the art. The scope of the invention, therefore, is to be determined by reference to the following claims:

The invention claimed is:

1. A personal monitor system for monitoring a safety of a person that might be exposed to a gas or other hazards while at a worksite or while traveling to or from the worksite, the personal monitor system comprising:

a central base system;

a portable transceiver unit carried by the person and being movable thereby to a remote location relative to the central base system, the portable transceiver unit includes a logic circuit;

a wireless communication link placing the portable transceiver unit in communication with the central base system;

a gas sensor borne by the portable transceiver unit, operatively coupled to the logic circuit, and being responsive to the gas;

a user interface borne by the portable transceiver unit, the user interface being operatively coupled to the logic circuit and being responsive to a plurality of manual manipulations by the person;

a notification system borne by the portable transceiver unit and being operatively coupled to the logic circuit;

an alarm emanating from the notification system if a concentration of the gas, as sensed by the gas sensor, exceeds a predetermined limit;

an alarm message displayed by the central base system as a result of the concentration of gas (as sensed by the gas sensor) exceeding the predetermined limit;

a plurality of prompt signals periodically emanating from the notification system, wherein the plurality of prompt signals includes a first prompt signal;

a first check-in signal conveyed by the wireless communication link from the portable transceiver unit to the central base system in response to a first manual manipulation of the user interface, wherein the first manual manipulation is one of the plurality of manual manipulations; and a warning message displayed by the central base system if the central base system fails to receive a subsequent check-in signal within a certain time span following at least one of the first check-in signal and the first prompt signal.

2. The personal monitor system of claim 1, further comprising a plurality of command signals conveyed by the wireless communication link from the central base system to the portable transceiver unit, the plurality of prompt signals at the portable transceiver unit being initiated by the plurality of command signals from the central base.

3. The personal monitor system of claim 1, wherein the plurality of prompt signals occur more frequently when the portable transceiver is at the worksite than when the portable transceiver is traveling to the worksite.

4. The personal monitor system of claim 1, further comprising a record provided by the central base system, the record identifying whether the portable transceiver unit is at the worksite or traveling thereto.

5. The personal monitor system of claim 1, wherein the user interface comprises a push button that, depending on how many times the push button is depressed in succession, indicates whether the person is calling for help or the person is okay.

6. The personal monitor system of claim 1, wherein the user interface comprises a push button that, depending on how many times the push button is depressed in succession, indicates whether the portable transceiver unit is traveling beyond the worksite or is at the worksite.

7. A personal monitor method that involves the use of a central base system and a portable transceiver unit for monitoring a safety of a person that might be exposed to a gas or other hazards while at a worksite or while traveling to or from the worksite, wherein the worksite is at a remote location relative to the central base system, the personal monitor method comprising:
   during a chosen period of monitoring, maintaining the portable transceiver unit in proximity with the person such that the portable transceiver unit and the person generally travel and move with each other during the chosen period of monitoring;
   at least periodically establishing wireless communication between the portable transceiver unit and the central base system;
   sensing the gas via a gas sensor borne by the portable transceiver unit;
   the portable transceiver unit notifying the person when a concentration of the gas exceeds a predetermined limit;
   during a first period within the chosen period of monitoring, the person and the portable transceiver unit traveling to the worksite;
   during a second period within the chosen period of monitoring, the person and the portable transceiver unit moving with each other at the worksite;
   at least one of the portable transceiver unit and the central base determining whether the portable transceiver unit is traveling to the worksite or is at the worksite; and
   the portable transceiver unit periodically prompting the person to manually manipulate a user interface on the transceiver unit when the portable transceiver unit is at the worksite.

8. The personal monitor method of claim 7, further comprising the central base system commanding that the portable transceiver unit is to prompt the person to manually manipulate the user interface on the transceiver unit.

9. The personal monitor method of claim 7, wherein the prompting occurs less frequently, if at all, when the portable transceiver unit is traveling to the worksite than when the portable transceiver unit is at the worksite.

10. The personal monitor method of claim 7, further comprising prompting the person to manually manipulate the user interface on the portable transceiver unit when the portable transceiver unit is at a generally fixed location off the worksite.

11. The personal monitor method of claim 7, further comprising the person manipulating the user interface to create a signal that indicates that the portable transceiver unit has arrived at the worksite.

12. The personal monitor method of claim 7, further comprising the wireless communication link conveying a location signal from the portable transceiver unit to the central base system, wherein determining whether the portable transceiver unit is traveling to the worksite or is at the worksite is based on the location signal.

13. The personal monitor method of claim 7, wherein the user interface includes a push button, and further comprising the person selectively pressing the push button a first given number of times to indicate that the person has arrived at the worksite and pressing the push button a second given number of times to indicate that the person is departing the worksite, the given numbers being equal to at least one, the first given number being distinguishable from the second given number, and the person pressing the push button the given number in succession if the given number is greater than one.

14. The personal monitor method of claim 7, wherein the user interface includes a push button, and further comprising the person selectively pressing the push button a given number of times to indicate that the person is no longer at the worksite but instead is at a predetermined home location, the given number being equal to at least one, and the person pressing the push button the given number in succession if the given number is greater than one.

15. The personal monitor method of claim 14, further comprising:
   the wireless communication link repeatedly conveying a location signal from the portable transceiver unit to the central base system; and
   after pressing the push button the given number of times to indicate that the person is at the predetermined home location, determining (based on the location signal) whether the portable transceiver unit is traveling from the predetermined home location.

16. The personal monitor method of claim 7, wherein the user interface includes a push button, and further comprising the person selectively pressing the push button a first given number of times to indicate that the person is okay and pressing the push button a second given number of times to indicate that the person is requesting assistance, the given numbers being equal to at least one, the first given number being distinguishable from the second given number, and the person pressing the push button the given number in succession if the given number is greater than one.

17. The personal monitor method of claim 7, further comprising displaying a warning at the central base system in response to the person failing to manually manipulate the user interface in spite of the portable transceiver unit's prompting of the person to do so.

18. The personal monitor method of claim 7, wherein the user interface includes a push button, and further comprising:
   the person selectively pressing the push button a given number of times to indicate that the person is at the worksite, the given number being equal to at least one;
   the wireless communication link conveying a location signal from the portable transceiver unit to the central base system; and
   recording an association of the worksite and the location signal.

19. The personal monitor method of claim 7, further comprising:
   manipulating the user interface to send a first drill signal to the central base, the first drill signal indicating that a first drill is being initiated at the worksite, the first drill involving a first set of actions to be performed by a crew at the worksite;

prompting the crew to perform the first set of actions at the worksite;

manipulating the user interface to send a completion signal to the central base, the completion signal indicating that the crew completed the first set of actions at the worksite; and recording an occurrence of the first drill signal and the completion signal, thereby creating a first record that includes a date and time-of-day stamp associated with the first drill.

20. The personal monitor method of claim 19, further comprising:

manipulating the user interface to send a second drill signal to the central base, the second drill signal indicating that a second drill is being initiated at the worksite, the second drill involving a second set of actions to be performed by the crew at the worksite, the first drill being distinguishable from the second drill with the first set of actions being distinguishable from the second set of actions;

prompting the crew to perform the second set of actions at the worksite;

recording an occurrence of the second drill signal; and creating a second record that includes a second date and time-of-day stamp associated with the second drill.

21. The personal monitor method of claim 7, further comprising selectively manipulating the user interface in a first manner and a second manner with the first manner being for soliciting assistance related to a potential health problem and the second manner being for soliciting assistance related to a potential illegal activity.

22. A personal monitor method that involves the use of a central base system and a portable transceiver unit for monitoring a safety of a person that might be exposed to a gas or other hazards while at a worksite or while traveling to or from the worksite, wherein the worksite is at a remote location relative to the central base system, the personal monitor method comprising:

maintaining the portable transceiver unit in proximity with the person such that the portable transceiver unit and the person generally travel and move with each other;

at least periodically establishing wireless communication between the portable transceiver unit and the central base system;

sensing the gas via a gas sensor borne by the portable transceiver unit;

the portable transceiver unit notifying the person when a concentration of the gas exceeds a predetermined limit;

during a first period, the person and the portable transceiver unit traveling to the worksite;

during a second period, the person and the portable transceiver unit moving with each other at the worksite;

at least one of the portable transceiver unit and the central base system determining whether the portable transceiver unit is traveling to the worksite or is at the worksite;

the portable transceiver unit periodically prompting the person to push a push button on the transceiver unit when the portable transceiver unit is at the worksite;

the person selectively pressing the push button on the portable transceiver unit a first given number of times to indicate that the person has arrived at the worksite;

the person selectively pressing the push button a second given number of times to indicate that the person is departing the worksite;

the person selectively pressing the push button a third given number of times to indicate that the person is okay; and the person selectively pressing the push button a fourth given number of times to indicate that the person is requesting assistance, the given numbers being equal to at least one, the given numbers being distinguishable from each other, and the person pressing the push button the given number in succession if the given number is greater than one.

23. The personal monitor method of claim 22, wherein the prompting occurs less frequently, if at all, when the portable transceiver unit is traveling beyond the worksite than when the portable transceiver unit is at the worksite.

* * * * *